United States Patent
Pairoys (10) Patent No.: US 9,835,762 B2
(45) Date of Patent: Dec. 5, 2017

(54) PETROPHYSICAL ROCK CHARACTERIZATION

(71) Applicant: SCHLUMBERGER TECHNOLOGY CORPORATION, Sugar Land, TX (US)

(72) Inventor: Fabrice Pairoys, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 283 days.

(21) Appl. No.: 14/612,795

(22) Filed: Feb. 3, 2015

(65) Prior Publication Data

US 2015/0219789 A1 Aug. 6, 2015

Related U.S. Application Data (60) Provisional application No. 61/936,776, filed on Feb. 6, 2014.

(51) Int. Cl.
*G01V 9/00* (2006.01)
*G01N 15/08* (2006.01)
(Continued)

(52) U.S. Cl.
CPC .............. *G01V 9/00* (2013.01); *G01N 15/08* (2013.01); *G01N 27/041* (2013.01); *G01N 33/24* (2013.01)

(58) Field of Classification Search
CPC ........ G01V 9/00; G01N 15/08; G01N 27/041; G01N 33/24
See application file for complete search history.

(56) References Cited

U.S. PATENT DOCUMENTS

| | | | | |
|---|---|---|---|---|
| 2,345,935 A | * | 4/1944 | Hassler | G01N 15/0826 73/38 |
| 2,437,935 A | * | 3/1948 | Brunner | G01N 15/08 250/304 |

(Continued)

FOREIGN PATENT DOCUMENTS

WO 2004-019029 A1 3/2004

OTHER PUBLICATIONS

International Search Report and Written Opinion for corresponding PCT Application Serial No. PCT/US2015/014359, dated May 12, 2015, 9 pages.

(Continued)

*Primary Examiner* — John Fitzgerald (57) ABSTRACT

A full petrophysical rock characterization of a rock sample in a single workflow uses a separator containing two immiscible fluids. The fluids form a fluid interface. A video camera monitors the height of the fluid interface. Current electrodes and potential electrodes are electrically connected to the rock sample. An impedance meter makes measurements across the current electrodes and the potential electrodes. A tubing is attached to one end of the rock sample and to one end of the separator and transports one of the immiscible fluids therebetween. Another tubing is attached to the other end of the rock sample and to the separator and transports the other immiscible fluid therebetween. Yet another tubing transports an immiscible mixture of the immiscible fluids from the rock sample to the separator. Pressure gauges measures the pressures in the tubings. Pumps are disposed inline with the certain tubings.

20 Claims, 3 Drawing Sheets

(51) Int. Cl.
*G01N 33/24* (2006.01)
*G01N 27/04* (2006.01)

(56) References Cited

U.S. PATENT DOCUMENTS

| | | | | |
|---|---|---|---|---|
| 3,380,292 | A | * | 4/1968 | Le Fournier ............. G01N 1/36 166/250.16 |
| 3,590,923 | A | * | 7/1971 | Cooke, Jr. ............... E21B 49/00 166/252.6 |
| 4,907,448 | A | * | 3/1990 | Givens ................. G01N 33/241 324/376 |
| 4,924,187 | A | * | 5/1990 | Sprunt ................. G01N 33/241 324/376 |
| 5,146,086 | A | * | 9/1992 | De ......................... G01N 15/08 250/253 |
| 5,209,104 | A | * | 5/1993 | Collins ................ G01N 33/241 324/376 |
| 5,284,051 | A | * | 2/1994 | Laali ..................... G01N 33/241 73/152.39 |
| 5,297,420 | A | * | 3/1994 | Gilliland ................ G01N 15/08 73/38 |
| 5,363,006 | A | | 11/1994 | Yano et al. |
| 5,493,226 | A | * | 2/1996 | Honarpour ........... G01N 33/241 324/376 |
| 5,503,001 | A | | 4/1996 | Wong |
| 5,637,796 | A | * | 6/1997 | Deruyter ............ G01N 15/0806 73/152.09 |
| 5,679,885 | A | | 10/1997 | Lenormand et al. |
| 5,698,772 | A | * | 12/1997 | Deruyter ............ G01N 15/0826 73/152.07 |
| 2005/0178189 | A1 | | 8/2005 | Lenormand et al. |
| 2011/0185809 | A1 | | 8/2011 | Guieze et al. |
| 2014/0318232 | A1 | | 10/2014 | Pairoys |

OTHER PUBLICATIONS

Ramakrishnan et al, "A New Technique to Measure Static and Dynamic Properties of a Partially Saturated Porous , Medium", Chem. Eng. Sci. vol. 46., pp. 1157-1163.

Lenormand et al, "A Novel Method for the Determination of Water/Oil Capillary Pressure of Mixed Wettability Samples", 1993 SCA Conference, Paper No. 9322, 16 pages.

Li et al, "A Semianalytical Method to Calculate Relative Permeability from Resistivity Well Logs", SPE 95575, SPE Annual Technical Conference and Exhibition, Dallas, Oct. 9-12, 2005, 5 pages.

Pairoys et al, "Interrelationship between Resistivity and Relative Permeability of a Carbonate Rock during Drainage and Imbibition Experiments", 2013 SCA Conference, pp. 16-19.

* cited by examiner

FIG. 1

PROVIDE: A SEPARATOR CONTAINING TWO IMMISCIBLE FLUIDS, WHEREIN THE TWO IMMISCIBLE FLUIDS COMPRISE A LOWER FLUID, AN UPPER FLUID, AND A FLUID INTERFACE; AN OPTICAL MEASUREMENT DEVICE THAT MONITORS THE HEIGHT OF THE FLUID INTERFACE; A ROCK SAMPLE; TWO OR MORE CURRENT ELECTRODES IN ELECTRICAL CONTACT WITH THE ROCK SAMPLE; TWO OR MORE POTENTIAL ELECTRODES IN ELECTRICAL CONTACT WITH THE ROCK SAMPLE; AN IMPEDANCE MEASUREMENT DEVICE IN ELECTRICAL CONTACT WITH THE TWO OR MORE CURRENT ELECTRODES AND THE TWO OR MORE POTENTIAL ELECTRODES; A FIRST TUBING SEALINGLY ENGAGED TO A FIRST END OF THE ROCK SAMPLE AND ALLOWING FOR FLUID COMMUNICATION OF THE LOWER FLUID BETWEEN THE FIRST END OF THE ROCK SAMPLE AND A LOWER END OF THE SEPARATOR; A SECOND TUBING SEALINGLY ENGAGED TO A SECOND END OF THE ROCK SAMPLE, ALLOWING FOR FLUID COMMUNICATION OF THE UPPER FLUID BETWEEN THE SECOND END OF THE ROCK SAMPLE AND AN UPPER END OF THE SEPARATOR; A THIRD TUBING SEALINGLY ENGAGED TO THE SECOND END OF THE ROCK SAMPLE, ALLOWING FOR FLUID COMMUNICATION OF AN IMMISCIBLE MIXTURE OF THE UPPER FLUID AND THE LOWER FLUID BETWEEN THE SECOND END OF THE ROCK SAMPLE AND AN INTERMEDIATE PORTION OF THE SEPARATOR; ONE OR MORE PRESSURE GAUGES, WHEREIN EACH PRESSURE GAUGE MONITORS THE PRESSURE IN AT LEAST ONE OF THE TUBINGS; A FIRST PUMP INLINE WITH THE FIRST TUBING; AND A SECOND PUMP INLINE WITH THE SECOND TUBING ~202

↓

PERFORM A FULL PETROPHYSICAL ROCK CHARACTERIZATION ON THE ROCK SAMPLE IN A SINGLE WORKFLOW USING A COMBINATION OF TECHNIQUES SELECTED FROM THE GROUP CONSISTING OF THE SEMI-DYNAMIC METHOD, DARCY'S LAW FOR TWO IMMISCIBLE PHASE FLOW, THE RAMAKRISHNAN AND CAPPIELLO'S EXPRESSION, LI'S MODEL FOR PRIMARY DRAINAGE, PAIROYS' MODEL FOR IMBIBITION, THE BROOKS-COREY EQUATION, PAIROYS' NORMALIZED RESISTIVITY MODEL, AND ARCHIE'S LAW ~204

PETROPHYSICAL ROCK CHARACTERIZATION

CROSS-REFERENCE TO RELATED APPLICATIONS

This application claims, under 35 U.S.C. §119, priority to and the benefit of U.S. Provisional Patent Application No. 61/936,776, filed Feb. 6, 2014.

BACKGROUND OF THE DISCLOSURE

There are many important petrophysical parameters used to interpret fluid flow in reservoirs and for calibrating appropriate reservoir simulation models. Among these are relative permeability, capillary pressure, saturation, spontaneous displacement, wettability, and resistivity, to name a few. In general, any one of those parameter can have different values during different modes of production such as the primary drainage mode, the imbibition mode, and the secondary drainage mode. The various parameter values for those different modes are conventionally determined (if at all) in the lab using two separate, time-consuming core flooding experiments. In addition to being time and labor intensive, a particular core sample can change during one of the experiments and adversely affect the results of the other.

In the prior art, there is no single experiment that allows one to determine all of those various parameter values. All those parameters are determined independently in the lab using special core analysis. Because the measurements are made during different experiments, using time-consuming methods, a full set of data on one single core plug can take a year or more to obtain. To run the different core flooding tests on the same sample, core cleanings are required, increasing the experimental time. It is generally preferred to run the complete experimental program on several core samples with similar properties, but it is difficult to ensure the different samples will behave similarly.

One method, known as the "semi-dynamic method", allows one to obtain reliable estimates of many of those parameters. For example, the semi-dynamic method can be used to determine the capillary pressure for all three of the mentioned production modes, but determines the relative permeability for only certain modes. In addition, certain parameters, such as the relative permeability, is determined for each fluid present in the sample, typically brine and oil. Another method, referred to herein as "Li's relationship" or "Li's model" uses resistivity measurements to determine the relative permeability of conductive fluids such as brine. Other relationships, such as "Darcy's law for two immiscible phase flow", the "Ramakrishan and Cappiello expression", the "Brooks-Corey equation", Pairoys' model for imbibition, and still others are known and used to determine certain parameter values. Each of those various relationships will be discussed further in the detailed description below. Obtaining all values for all stated parameters is referred to generally and herein as a "full petrophysical rock characterization".

SUMMARY

A full petrophysical rock characterization of a rock sample in a single workflow uses a separator containing two immiscible fluids. The fluids form a fluid interface. A video camera monitors the height of the fluid interface. Current electrodes and potential electrodes are electrically connected to the rock sample. An impedance meter makes measurements across the current electrodes and the potential electrodes. A tubing is attached to one end of the rock sample and to one end of the separator and transports one of the immiscible fluids therebetween. Another tubing is attached to the other end of the rock sample and to the separator and transports the immiscible fluid therebetween. Yet another tubing transports an immiscible mixture of the immiscible fluids from the rock sample to the separator. Pressure gauges measures the pressures in the tubings. Pumps are disposed inline with the certain tubings.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Embodiments are described with reference to the following figures. The same numbers are generally used throughout the figures to reference like features and components.

FIG. 2 is a flowchart to perform a full petrophysical rock characterization in a single experiment, in accordance with the present disclosure.

DETAILED DESCRIPTION

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms "above" and "below", "up" and "down", "upper" and "lower", "upwardly" and "downwardly", and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate. It will also be understood that, although the terms first, second, etc. may be used herein to describe various elements, these elements should not be limited by these terms. These terms are only used to distinguish one element from another.

The terminology used in the description herein is for the purpose of describing particular embodiments only and is not intended to be limiting. As used in the description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

A system and method to perform a full petrophysical rock characterization in a single experiment or workflow is described herein. For definiteness, a full petrophysical rock characterization, as used herein, includes the determination of relative permeability, capillary pressure, Archie's cementation factor m and saturation exponent n, resistivity index, saturation, spontaneous displacement, and wettability index. At least some of those parameters have different values in different production modes (e.g., primary drainage, imbibition, and secondary drainage), and a full petrophysical rock characterization includes determining those different values as well.

Figure 1:
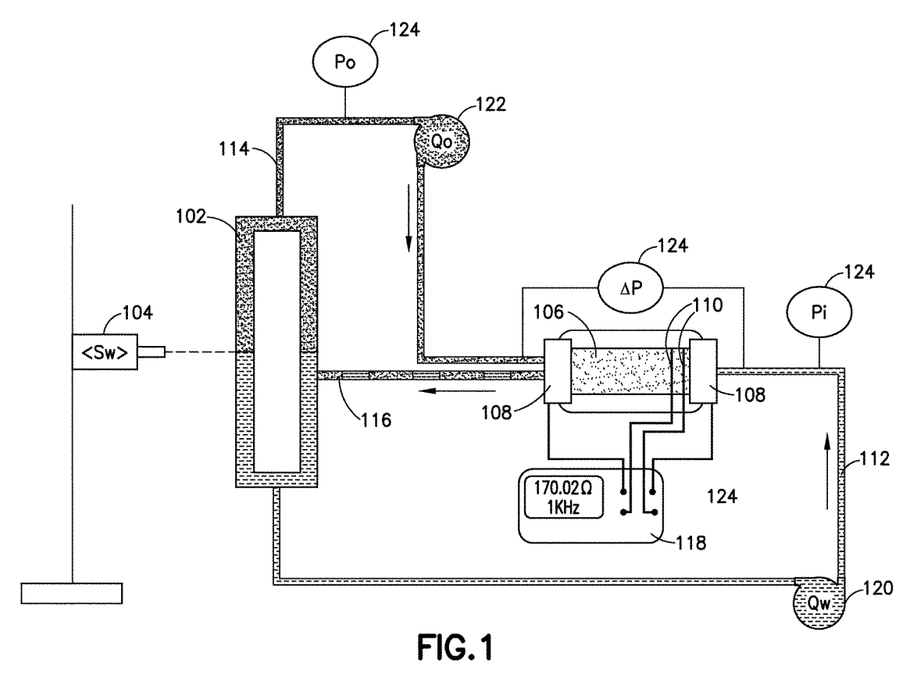
FIG. 1 is a schematic drawing showing an embodiment of an apparatus that may be used to perform a full petrophysical rock characterization in a single experiment, in accordance with the present disclosure.

FIG. 1 schematically shows one embodiment of an apparatus that may be used to perform a full petrophysical rock characterization. Two phases (i.e., fluids) of different densities or otherwise immiscible are shown in a separator 102. For that reason this is considered a two-phase flow experiment. For ease of discussion, we shall assume the two phases are water (brine) and oil. Separator 102 is generally a columnar structure such as the union of two U-tubes, one of them inverted relative to the other, to exploit gravity. The higher density brine tends to settle in separator 102 and is the lower phase, while the lower density oil rides atop the brine and is the upper phase. A video level tracker 104 monitors the height of the interface between the two phases. That provides an optical measurement of the average water saturation.

A rock sample 106 is configured with four electrodes: two current electrodes 108 and two potential electrodes 110. The current electrodes 108 are joined to opposite ends of rock sample 106. The two potential electrodes 110 are joined to rock sample 106 at desired intermediate locations, far enough away from the ends to avoid any end effects. In the embodiment shown, potential electrodes 110 are spaced 2.54 cm apart (as measured along a longitudinal axis joining the two current electrodes 108). The particular current electrode 108 attached to a first end of rock sample 106 is adapted to allow a single first tubing 112 conveying one of the phases to sealingly engage the first end of rock sample 106. The particular current electrode 108 attached to a second end (opposite the first end) of rock sample 106 is adapted to allow two separate tubings, second tubing 114 and third tubing 116, second tubing 114 conveying the other of the two phases and third tubing 116 conveying an immiscible mixture of the two phases, to sealingly engage the second end of rock sample 106. An impedance meter 118 is electrically connected to the electrodes to make electrical measurements. Rock sample 106 may be, for example, a rock slab or a core plug.

First tubing 112 is attached to the lower end of separator 102 and is in fluid communication with the lower phase in separator 102. A brine pump 120 is provided inline with first tubing 112 to provide pressure to the brine. Similarly, second tubing 114 is attached to the upper end of separator 102 and is in fluid communication with the upper phase in separator 102. An oil pump 122 is provided inline with second tubing 114 to provide pressure to the oil. Finally, third tubing 116 is in fluid communication with separator 102. Thus, two flow loops are created, the first flow loop comprising first tubing 112, rock sample 106, third tubing 116, and separator 102. The second flow loop comprises second tubing 114, rock sample 106, third tubing 116, and separator 102. Various pressure gauges 124 are used to monitor the differential pressure (i.e., the pressure difference between the first end and the second end of rock sample 106), as well as the pressures output by brine pump 120 and oil pump 122.

FIG. 1 shows flow directions corresponding to the imbibition mode or cycle. The experiment is run at ambient conditions (i.e., room temperature and atmospheric pressure) while testing in this mode. The first flow loop shows brine being injected into an inlet face of rock sample 106. The second flow loop shows oil recirculation at an outlet face of rock sample 106. Both of those flow loops share the common third tubing 116 to transport the two-phase mixture from the outlet face of rock sample 106 to separator 102.

Thus, in this mode, brine is injected at the inlet face and through the sample while oil is recirculated at the outlet face. This is similar to what is done in what is known as the "unsteady-state method". A particular flow rate is applied and the system is allowed to equilibrate. Measurements such as differential pressure and production are made once the system equilibrates. This is similar to what is done in a method known as the "steady-state method". Resistivity measurements are also made once the system equilibrates. Once all measurements on the equilibrated system are complete, a different flow rate is applied and the process is repeated. This is done for several different flow rates.

The apparatus of FIG. 1 fully incorporates and is able to perform the semi-dynamic method. The semi-dynamic method may be used to determine many of the desired parameter values. The principle underlying the semi-dynamic method is the balance between the capillary pressure and the viscous pressure drop. The method combines aspects of a multi-rate unsteady-state experiment and a steady-state experiment. However, the semi-dynamic method does not incorporate resistivity measurements, as does the embodiment of FIG. 1.

In the following, reference is made to injected fluid and displaced/recirculated fluid. The fluid which is being injected and displaced/recirculated depends on the production mode or cycle.

Using the semi-dynamic method, the inlet capillary pressure $Pc_{inlet}$ may be directly obtained from the pressure drop in the injected fluid. When production of the displaced fluid ceases, the pressure in this fluid is constant along the core sample and equal to the outlet pressure, which is controlled by the pressure of the recirculated fluid. Thus, the pressure drop of the displaced/recirculated fluid is zero. As a result, the pressure gradient in the injected fluid is equal to the gradient of capillary pressure. In other words, the pressure drop $\Delta P$ across rock sample 106 is equal to the inlet capillary pressure $Pc_{inlet}$.

Inlet Capillary Pressure $Pc_{inlet}$ Calculation
(Injected Fluid is Fluid 1 and Displaced/Recirculated Fluid is Fluid 2):

$$Pc = P_{fluid1} - P_{fluid2} \qquad \text{Eq. 1}$$

$$\frac{dPc}{dx} = \frac{dP_{fluid1}}{dx} - \frac{dP_{fluid2}}{dx} \qquad \text{Eq. 2}$$

where x is the coordinate along the length of rock sample 106. At equilibrium (end of each flow rate step), $P_{fluid2}$ is constant. Then:

$$\frac{dPc}{dx} = \frac{dP_{fluid1}}{dx} \qquad \text{Eq. 3}$$

since $$\frac{dP_{fluid2}}{dx} = 0$$

By integration of Equation 3, we obtain:

$$Pc_{outlet} - Pc_{inlet} = P_{fluid1\ outlet} - P_{fluid1\ inlet} \qquad \text{Eq. 4}$$

It is also assumed that the capillary pressure at the outlet $Pc_{outlet}$ is zero, thus:

$$\Delta P = P_{fluid1\ inlet} - P_{fluid1\ outlet} = \Delta P_{fluid1} = Pc_{inlet} \qquad \text{Eq. 5}$$

Inlet Relative Permeability $Kr_{inlet}$ Calculation:

The relative permeability of the injected fluid at the inlet face can be directly determined from Darcy's law for two immiscible phase flow.

$$Kr_{fluid1} = \frac{\mu_{fluid1} L}{KA} \frac{dQ_{fluid1}}{dPc_{inlet}} \qquad \text{Eq. 6}$$

where $Q_{fluid1}$ is the flow rate of fluid 1, $\mu_{fluid1}$ is the viscosity of fluid 1, K is the base or absolute permeability to brine, $Pc_{inlet}$ is the inlet capillary pressure, and L and A are, respectively, the length and the cross-sectional area of the rock sample. The inlet relative permeability of the injected fluid 1 can be obtained from the slope of $Q_{fluid1}$ plotted against $Pc_{inlet}$.

Inlet Saturation $S_{fluid2inlet}$ Calculation:
The inlet saturation of the displaced fluid can be obtained from the Ramakrishnan and Cappiello's expression:

$$S_{fluid2inlet} = \langle S_{fluid2} \rangle + Q_{fluid1} \frac{d\langle S_{fluid2} \rangle}{dQ_{fluid1}} \qquad \text{Eq. 7}$$

The inlet saturation $S_{fluid2\ inlet}$ of the displaced fluid 2 can be obtained from the slope of $S_{fluid2}$ plotted against $Q_{fluid1}$. The bracketed saturation term means the average saturation of fluid 2.

At this stage, the relative permeability of the displaced phase is still unknown. One technique to obtain it is to use Li's model for primary drainage. Another technique is Pairoys' model for imbibition. Both approaches are based on rock electrical measurements. As stated earlier, the resistivity response of rock sample 106 is measured at equilibrium.

Brine-Oil Relative Permeability in Primary Drainage:

Rock sample 106 is initially saturated with brine which is the conductive phase for electrical measurements. In the previous equations, brine is the displaced fluid 2 in drainage. Because the conductive phase or brine relative permeability is inversely proportional to Archie's resistivity index RI, Li derived a relationship between relative permeability of the wetting phase and resistivity index RI during a primary drainage cycle:

$$Krw = Sw^* \cdot \frac{1}{RI} \qquad \text{Eq. 8}$$

where Krw is the conductive phase (brine) relative permeability, RI is the resistivity index, and Sw* is the normalized saturation of the wetting phase in primary drainage defined as:

$$Sw^* = \frac{Sw - Swi}{1 - Swi} \qquad \text{Eq. 9}$$

where Sw is the water saturation (or conductive phase) and Swi is the irreducible water saturation. The "un-normalization" step is not required in primary drainage since Krw=1 at Sw=1 and Krw=0 at Swi. The relative permeability of the other phase (oil for instance) or injected fluid 1, Kro, is obtained from Equation 6:

$$Kro = \frac{\mu_o L}{KA} \frac{dQ_o}{dPc_{inlet}} \qquad \text{Eq. 10}$$

where $Q_o$ is the flow rate of the oil phase and $\mu_o$ is the viscosity of the oil phase.

Brine-Oil Relative Permeability in Imbibition:
For the imbibition cycle, the injected phase (brine injection) relative permeability Krw is obtained from Equation 6:

$$Krw = \frac{\mu_w L}{KA} \frac{dQ_w}{dPc_{inlet}} \qquad \text{Eq. 11}$$

where $Q_w$ is the flow rate of the brine phase and $\mu_w$ is the viscosity of the brine phase. Alternatively, Krw may be computed using Pairoys' model for imbibition:

$$Krw = Sw^*/RI^* \qquad \text{Eq. 12}$$

where RI*=RI/RI$_{min}$ and Sw*=(Sw−Swi)/(1−Swi−Sor). Here RI* is the effective resistivity index and RI$_{min}$ is the minimum resistivity index obtained at residual oil saturation Sor.

For the displaced phase (oil) relative permeability Kro, Pairoys' normalized resistivity model may be used:

$$Kro = (1 - Sw^*)RI^*$$  Eq. 13
$$= (1 - Sw^*)\frac{RI}{RI_{max}}$$

where here RI* is the normalized resistivity index and RI$_{max}$ is the maximum resistivity index at Swi.

Archie's law serves as the basis to determine the porosity and saturation of the formation from resistivity measurements as follows:

$$\frac{R_c}{R_f} = \frac{1}{\phi^m S_w^n}$$  Eq. 14 where $R_c$ is the resistivity of the rock, $R_f$ is the resistivity of the fluid in the pores, $\phi$ is the porosity, $S_w$ is the water saturation, and m and n are the Archie's empirical exponents. Resistivity index curves can be obtained from the resistivity measurements and the saturation exponent n can also be calculated.

Because certain of the above techniques requires electrical measurements, this approach cannot be directly applied when there is no conductive phase (e.g., when gas and oil are the two phases). To get the imbibition Kro without using electrical measurement, the Brooks-Corey equation may be used:

$$Kro=(1-Sw^*)^2[1-(Sw^*)^{(2+\lambda)/\lambda}]$$  Eq. 15 where $\lambda$ is the pore size distribution index and is directly obtained from the slope of the log-log plot of the capillary pressure Pc versus water saturation Sw.

By taking the base permeability equal to the effective permeability to oil Ko(Swi), the "un-normalization" step is also not required in imbibition since Kro(Swi)=1 and Kro(Sor)=0. (Sor is the residual oil saturation (or non-conductive phase)). Because capillary pressure Pc can be directly obtained during primary drainage, imbibition, and secondary drainage cycles (and the spontaneous displacement can be obtained during secondary drainage and imbibition cycles), USBM and Amott-Harvey wettability indices WI can also been determined. The wettability index can help one understand the flow behaviors according to the wettability of the rock.

Attention is now directed to processing procedures, methods, techniques, and workflows that are in accordance with some embodiments. Some operations in the processing procedures, methods, techniques, and workflows disclosed herein may be combined and/or the order of some operations may be changed. It is important to recognize that geologic interpretations, sets of assumptions, and/or domain models may be refined in an iterative fashion. This concept is applicable to the processing procedures, methods, techniques, and workflows discussed herein. This iterative refinement can include use of feedback loops executed on an algorithmic basis, such as at a computing device and/or through manual control by a user who may make determinations regarding whether a given step, action, template, or model has become sufficiently accurate.

FIG. 2 shows a flowchart illustrating an embodiment in accordance with this disclosure. In this embodiment, the workflow comprises: providing a separator containing two immiscible fluids, wherein the two immiscible fluids comprise a lower fluid, an upper fluid, and a fluid interface; an optical measurement device that monitors the height of the fluid interface; a rock sample; two or more current electrodes in electrical contact with the rock sample; two or more potential electrodes in electrical contact with the rock sample; an impedance measurement device in electrical contact with the two or more current electrodes and the two or more potential electrodes; a first tubing sealingly engaged to a first end of the rock sample and allowing for fluid communication of the lower fluid between the first end of the rock sample and a lower end of the separator; a second tubing sealingly engaged to a second end of the rock sample, allowing for fluid communication of the upper fluid between the second end of the rock sample and an upper end of the separator; a third tubing sealingly engaged to the second end of the rock sample, allowing for fluid communication of an immiscible mixture of the upper fluid and the lower fluid between the second end of the rock sample and an intermediate portion of the separator; one or more pressure gauges, wherein each pressure gauge monitors the pressure in at least one of the tubings; a first pump inline with the first tubing; and a second pump inline with the second tubing (202); and performing a full petrophysical rock characterization on the rock sample in a single workflow using a combination of techniques selected from the group consisting of the semi-dynamic method, Darcy's law for two immiscible phase flow, the Ramakrishnan and Cappiello's expression, Li's model for primary drainage, Pairoys' model for imbibition, the Brooks-Corey equation, Pairoys' normalized resistivity model, and Archie's law (204). Thus, using the described workflow, all petrophysical parameters can be determined on a single rock sample 106 by running primary drainage, imbibition, and secondary drainage cycles, on one single experiment, without unloading the sample. This allows for a full two-phase flow description of a rock.

Figure 3:
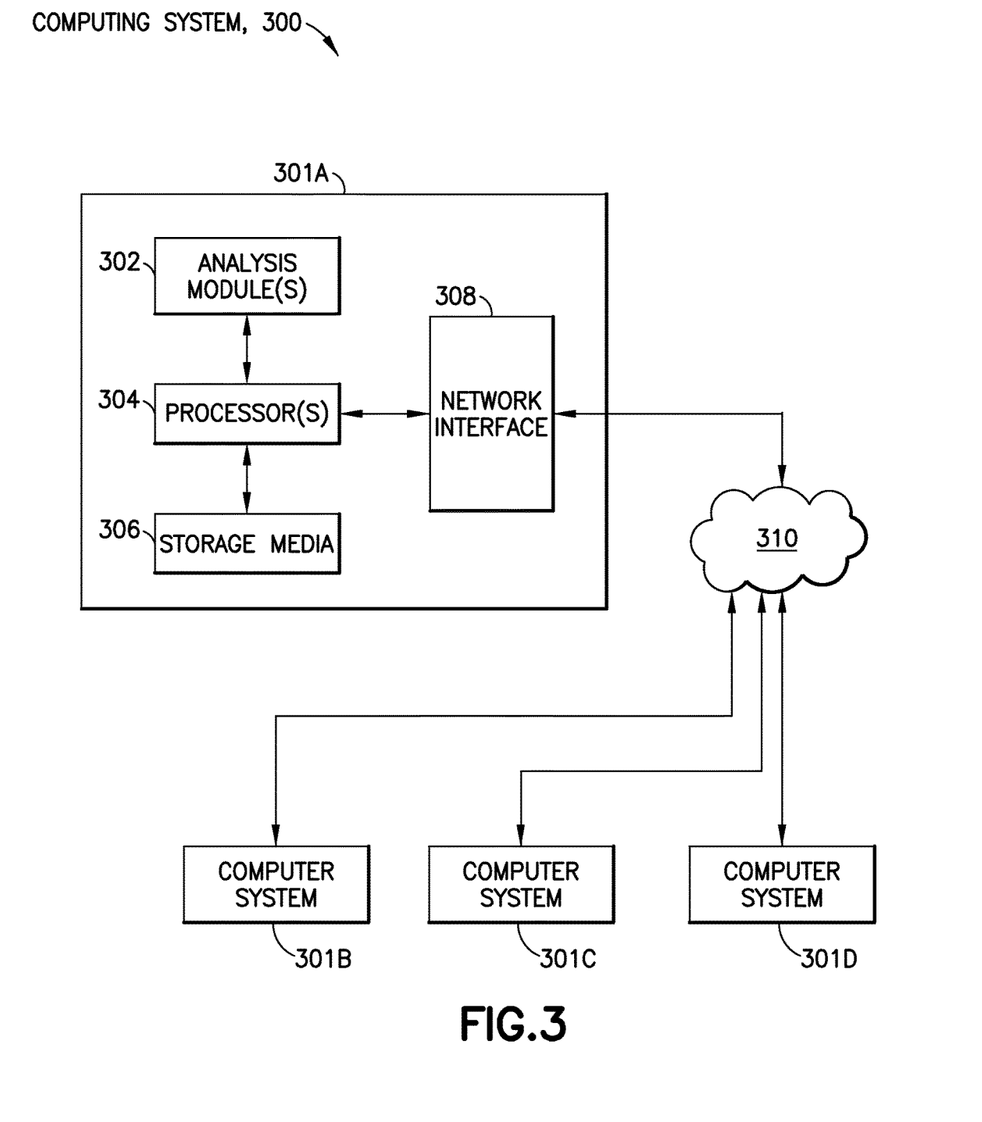
FIG. 3 illustrates an example computing system usable for one or more disclosed embodiments, in accordance with the present disclosure.

The computing system 300 shown in FIG. 3 can be an individual computer system 301A or an arrangement of distributed computer systems. The computer system 301A includes one or more analysis modules 302 that are configured to perform various tasks according to some embodiments, such as one or more methods disclosed herein (e.g., any of the steps, methods, techniques, and/or processes, and/or combinations and/or variations and/or equivalents thereof). To perform those various tasks, analysis module 302 operates independently or in coordination with one or more processors 304 that is (or are) connected to one or more storage media 306. The processor(s) 304 is (or are) also connected to a network interface 308 to allow the computer system 301A to communicate over a data network 310 with one or more additional computer systems and/or computing systems, such as 301B, 301C, and/or 301D (note that computer systems 301B, 301C, and/or 301D may or may not share the same architecture as computer system 301A, and may be located in different physical locations, while in communication with one or more computer systems such as 301C and/or 301D that are located in one or more data centers onshore, on other ships, and/or located in various countries on different continents).

The storage media 306 can be implemented as one or more computer-readable or machine-readable storage media. Note that while in the example embodiment of FIG.

3 storage media 306 is depicted as within computer system 301A, in some embodiments, storage media 306 may be distributed within and/or across multiple internal and/or external enclosures of computing system 301A and/or additional computing systems. Storage media 306 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

It should be appreciated that computing system 300 is only one example of a computing system, and that computing system 300 may have more or fewer components than shown, may combine additional components not depicted in the example embodiment of FIG. 3, and/or computing system 300 may have a different configuration or arrangement of the components depicted in FIG. 3. For example, though not shown explicitly, computing system 300 would generally include input and output devices such as a keyboard, a mouse, a display monitor, and a printer and/or plotter. The various components shown in FIG. 3 may be implemented in hardware, software, or a combination of both hardware and software, including one or more signal processing and/or application specific integrated circuits.

A processor can include a microprocessor, microcontroller, processor module or subsystem, programmable integrated circuit, programmable gate array, or another control or computing device. Further, the steps in the processing methods described above may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of this disclosure.

Some of the embodiments described above can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). At least some of the embodiments described above can be implemented using such logic devices.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions, and alterations herein without departing from the scope of the present disclosure.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. An apparatus, comprising:
   a separator containing two immiscible fluids, wherein the two immiscible fluids comprise a lower fluid and an upper fluid, and form a fluid interface;
   an optical measurement device that monitors the height of the fluid interface;
   a rock sample;
   two or more current electrodes in electrical contact with the rock sample;
   two or more potential electrodes in electrical contact with the rock sample;
   an impedance measurement device in electrical contact with the two or more current electrodes and the two or more potential electrodes;

a first tubing sealingly engaged to a first end of the rock sample and allowing for fluid communication of the lower fluid between the first end of the rock sample and a lower end of the separator;

a second tubing sealingly engaged to a second end of the rock sample, allowing for fluid communication of the upper fluid between the second end of the rock sample and an upper end of the separator;

a third tubing sealingly engaged to the second end of the rock sample, allowing for fluid communication of an immiscible mixture of the upper fluid and the lower fluid between the second end of the rock sample and an intermediate portion of the separator;

one or more pressure gauges, wherein each pressure gauge monitors the pressure in at least one of the tubings;

a first pump inline with the first tubing; and a second pump inline with the second tubing.

2. The apparatus of claim 1, wherein the two immiscible fluids have different densities.

3. The apparatus of claim 1, wherein the lower fluid is brine and the upper fluid is oil.

4. The apparatus of claim 1, wherein the rock sample is from a subsurface formation.

5. The apparatus of claim 1, wherein the two or more potential electrodes are located away from the ends of the rock sample to avoid end effects.

6. The apparatus of claim 1, wherein one of the current electrodes is attached to the first end of the rock sample and another of the current electrodes is attached to the second end of the rock sample.

7. The apparatus of claim 6, wherein the first tubing is joined to the current electrode attached to the first end of the rock sample.

8. The apparatus of claim 6, wherein the second tubing and the third tubing are joined to the current electrode attached to the second end of the rock sample.

9. A method, comprising:

providing the apparatus of claim 1;

performing a full petrophysical rock characterization on the rock sample in a single workflow using a combination of techniques selected from the group consisting of: semi-dynamic method, Darcy's law for two immiscible phase flow, Ramakrishnan and Cappiello's expression, Li's model for primary drainage, Pairoys' model for imbibition, the Brooks-Corey equation, Pairoys' normalized resistivity model, and Archie's law.

10. The method of claim 9, wherein the semi-dynamic method comprises an unsteady-state method and a steady-state method.

11. The method of claim 9, wherein the full petrophysical rock characterization includes determination of relative permeability, capillary pressure, Archie's cementation factor m and saturation exponent n, resistivity index, saturation, spontaneous displacement, and wettability index for all production modes.

12. The method of claim 11, wherein the production modes include a primary drainage cycle, an imbibition cycle, and a secondary drainage cycle.

13. The method of claim 9, wherein the performing a full petrophysical rock characterization comprises, for one or more sets of flow rates, using a particular set of flow rates until flows equilibrate, making measurements while the flows are in equilibrium, and repeating using another of the one or more sets of flow rates until all sets of flow rates have been used.

14. The method of claim 13, wherein the type of measurements made are selected from the group consisting of: electrical resistivity, electrical impedance, tubing pressure, differential pressure, and height of the fluid interface.

15. A system, comprising:

an apparatus as claimed in claim 1; and a processor carried on the apparatus capable of:

performing a full petrophysical rock characterization on the rock sample in a single workflow using a combination of techniques selected from the group consisting of: semi-dynamic method, Darcy's law for two immiscible phase flow, the Ramakrishnan and Cappiello's expression, Li's model for primary drainage, Pairoys' model for imbibition, the Brooks-Corey equation, Pairoys' normalized resistivity model, and Archie's law.

16. The system of claim 15, wherein the semi-dynamic method comprises an unsteady-state method and a steady-state method.

17. The system of claim 15, wherein the full petrophysical rock characterization includes determination of relative permeability, capillary pressure, Archie's cementation factor m and saturation exponent n, resistivity index, saturation, spontaneous displacement, and wettability index for all production modes.

18. The system of claim 17, wherein the production modes include a primary drainage cycle, an imbibition cycle, and a secondary drainage cycle.

19. The system of claim 15, wherein the performing a full petrophysical rock characterization comprises, for one or more sets of flow rates, using a particular set of flow rates until flows equilibrate, making measurements while the flows are in equilibrium, and repeating using another of the one or more sets of flow rates until all sets of flow rates have been used.

20. The system of claim 19, wherein the type of measurements made are selected from the group consisting of electrical resistivity, electrical impedance, tubing pressure, differential pressure, and height of the fluid interface.

* * * * *